United States Patent
Berner et al.

(10) Patent No.: US 8,333,992 B2
(45) Date of Patent: *Dec. 18, 2012

(54) GASTRIC RETAINED GABAPENTIN DOSAGE FORM

(75) Inventors: Bret Berner, Half Moon Bay, CA (US); Sui Yuen Eddie Hou, Foster City, CA (US); Gloria M. Gusler, Cupertino, CA (US)

(73) Assignee: Depomed, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/560,938

(22) Filed: Jul. 27, 2012

(65) Prior Publication Data

US 2012/0289601 A1    Nov. 15, 2012

Related U.S. Application Data

(63) Continuation of application No. 12/749,101, filed on Mar. 29, 2010, now Pat. No. 8,252,332, which is a continuation of application No. 12/239,591, filed on Sep. 26, 2008, now Pat. No. 7,731,989, which is a continuation of application No. 10/280,309, filed on Oct. 25, 2002, now Pat. No. 7,438,927.

(60) Provisional application No. 60/335,248, filed on Oct. 25, 2001.

(51) Int. Cl.
*A61K 9/22* (2006.01)
*A61K 9/24* (2006.01)
*A61K 9/52* (2006.01)

(52) U.S. Cl. ......... 424/473; 424/457; 424/468; 424/484

(58) Field of Classification Search ..................... None
See application file for complete search history.

(56) References Cited

U.S. PATENT DOCUMENTS

| | | | |
|---|---|---|---|
| 3,574,820 A | 4/1971 | Johnson et al. | |
| 3,845,770 A | 11/1974 | Theeuwes et al. | |
| 3,977,404 A | 8/1976 | Theeuwes | |
| 4,024,175 A | 5/1977 | Satzinger et al. | |
| 4,087,544 A | 5/1978 | Satzinger et al. | |
| 4,152,326 A | 5/1979 | Hartenstein et al. | |
| 4,309,406 A | 1/1982 | Guley et al. | |
| 4,404,183 A | 9/1983 | Kawata et al. | |
| 4,462,839 A | 7/1984 | McGinley et al. | |
| 4,612,008 A | 9/1986 | Wong et al. | |
| 4,753,801 A | 6/1988 | Oren et al. | |
| 4,828,836 A | 5/1989 | Elger et al. | |
| 4,851,232 A | 7/1989 | Urquhart et al. | |
| 4,871,548 A | 10/1989 | Edgren et al. | |
| 4,894,476 A | 1/1990 | Butler et al. | |
| 4,996,058 A | 2/1991 | Sinnreich et al. | |
| 5,007,790 A | 4/1991 | Shell | |
| 5,084,479 A * | 1/1992 | Woodruff .................... | 514/530 |
| 5,232,704 A | 8/1993 | Franz et al. | |
| 5,273,758 A | 12/1993 | Royce | |
| 5,382,435 A | 1/1995 | Geary et al. | |
| 5,443,843 A | 8/1995 | Curatolo et al. | |
| 5,558,879 A | 9/1996 | Chen et al. | |
| 5,582,837 A | 12/1996 | Shell | |
| 5,591,452 A | 1/1997 | Miller et al. | |
| 5,660,861 A | 8/1997 | Jao et al. | |
| 5,783,212 A | 7/1998 | Fassihi et al. | |
| 5,872,984 A | 2/1999 | Berglund et al. | |
| 5,906,832 A * | 5/1999 | Jao et al. ................... | 424/465 |
| 5,945,125 A | 8/1999 | Kim | |
| 5,955,103 A * | 9/1999 | Jao et al. ................... | 424/457 |
| 5,972,389 A | 10/1999 | Shell et al. | |
| 6,024,977 A | 2/2000 | Yatvin et al. | |
| 6,024,982 A | 2/2000 | Oshlack et al. | |
| 6,054,482 A | 4/2000 | Augart et al. | |
| 6,117,453 A | 9/2000 | Seth et al. | |
| 6,120,803 A | 9/2000 | Wong et al. | |
| 6,162,466 A | 12/2000 | Licht et al. | |
| 6,187,338 B1 * | 2/2001 | Caruso et al. ............... | 424/468 |
| 6,242,488 B1 | 6/2001 | Bueno et al. | |
| 6,255,526 B1 | 7/2001 | Pesachovich et al. | |
| 6,273,340 B1 | 8/2001 | Rivailler et al. | |
| 6,294,192 B1 | 9/2001 | Patel et al. | |
| 6,294,198 B1 * | 9/2001 | Vilkov ........................ | 424/465 |
| 6,294,690 B1 | 9/2001 | Deering et al. | |
| 6,310,098 B1 | 10/2001 | Guttuso, Jr. | |
| 6,333,352 B1 | 12/2001 | Derakhshan | |
| 6,340,475 B2 | 1/2002 | Shell et al. | |
| 6,346,270 B1 * | 2/2002 | Shivanand et al. ......... | 424/473 |
| 6,350,471 B1 | 2/2002 | Seth | |
| 6,451,808 B1 | 9/2002 | Cowles | |

(Continued)

FOREIGN PATENT DOCUMENTS

| | | |
|---|---|---|
| CA | 2220038 | 7/1999 |
| CA | 2143500 | 4/2007 |
| DE | 4432757 A1 | 3/1996 |
| EP | 0458751 A1 | 5/1991 |
| EP | 1118321 | 7/2001 |
| WO | WO 90/11757 A1 | 10/1990 |
| WO | WO 92/04013 A1 | 3/1992 |
| WO | WO 93/18755 A1 | 3/1992 |
| WO | WO 95/29665 A1 | 11/1995 |
| WO | WO 96/26718 A2 | 9/1996 |
| WO | WO 96/32097 A1 | 10/1996 |
| WO | WO 97/18814 A1 | 5/1997 |
| WO | WO 97/47285 A1 | 12/1997 |
| WO | WO 98/11879 A1 | 3/1998 |
| WO | WO 98/55107 A1 | 12/1998 |

(Continued)

OTHER PUBLICATIONS

U.S. Appl. No. 09/425,491, Shell et al.
U.S. Appl. No. 10/045,816, filed Oct. 25, 2001, Berner et al.
Adler, "Treatment of restless legs syndrome with gabapentin", Clin. Neuropharmacol., vol. 20, No. 2, pp. 148-151 (1997).
Andrews et al., "Gabapentin: a new agent for the management of epilepsy", Ann. Pharmacother., vol. 28, pp. 1188-1196 (1994).

(Continued)

*Primary Examiner* — Robert A Wax
*Assistant Examiner* — Olga V Tcherkasskaya
(74) *Attorney, Agent, or Firm* — Susanne Ottoboni; Susan L. Harlocker; McDermott Will & Emery LLP

(57) ABSTRACT

A method of treatment for epilepsy and other disease states is described, which comprises the delivery of gabapentin in a gastric retained dosage form.

27 Claims, 2 Drawing Sheets

U.S. PATENT DOCUMENTS

| | | | |
|---|---|---|---|
| 6,465,012 | B2 | 10/2002 | Vilkov |
| 6,488,962 | B1 | 12/2002 | Berner et al. |
| 6,488,964 | B2 | 12/2002 | Bruna et al. |
| 6,635,280 | B2 | 10/2003 | Shell et al. |
| 6,635,281 | B2 | 10/2003 | Wong et al. |
| 6,682,759 | B2 | 1/2004 | Lim et al. |
| 6,683,112 | B2 | 1/2004 | Chen et al. |
| 6,723,340 | B2 | 4/2004 | Gusler et al. |
| 7,438,927 | B2 | 10/2008 | Berner et al. |
| 7,612,112 | B2 | 11/2009 | Berner et al. |
| 7,731,989 | B2 | 6/2010 | Berner et al. |
| 8,119,166 | B2 | 2/2012 | Berner et al. |
| 8,192,756 | B2 | 6/2012 | Berner et al. |
| 2001/0004644 | A1* | 6/2001 | Levin ............................ 514/646 |
| 2001/0008889 | A1* | 7/2001 | Caruso et al. ................. 514/216 |
| 2001/0036943 | A1 | 11/2001 | Coe et al. |
| 2001/0043946 | A1 | 11/2001 | Vilkov |
| 2001/0046473 | A1 | 11/2001 | Besse |
| 2001/0055607 | A1* | 12/2001 | Levin ............................ 424/435 |
| 2002/0012679 | A1 | 1/2002 | Bruna et al. |
| 2002/0012680 | A1 | 1/2002 | Patel et al. |
| 2002/0082252 | A1 | 6/2002 | Hochman |
| 2002/0107208 | A1* | 8/2002 | Chen et al. ....................... 514/25 |
| 2002/0115705 | A1 | 8/2002 | Magnus-Miller et al. |
| 2002/0142050 | A1 | 10/2002 | Straub et al. |
| 2003/0031711 | A1 | 2/2003 | Fara et al. |
| 2003/0044466 | A1 | 3/2003 | Markey et al. |
| 2003/0064036 | A1 | 4/2003 | Petereit et al. |
| 2003/0091630 | A1 | 5/2003 | Louie-Helm et al. |
| 2003/0100611 | A1 | 5/2003 | Berner et al. |
| 2003/0104052 | A1 | 6/2003 | Berner et al. |
| 2003/0104053 | A1 | 6/2003 | Gusler et al. |
| 2003/0104062 | A1 | 6/2003 | Berner et al. |
| 2003/0133985 | A1 | 7/2003 | Louie-Helm et al. |
| 2003/0152622 | A1 | 8/2003 | Louie-Helm et al. |
| 2003/0181390 | A1 | 9/2003 | Gallop et al. |
| 2004/0062802 | A1 | 4/2004 | Hermelin |
| 2004/0180088 | A1 | 9/2004 | Dudhara et al. |
| 2004/0185105 | A1 | 9/2004 | Berner et al. |
| 2005/0064036 | A1 | 3/2005 | Berner et al. |
| 2005/0158380 | A1 | 7/2005 | Chawla et al. |
| 2006/0094785 | A1 | 5/2006 | Guttoso, Jr. |
| 2006/0159743 | A1 | 7/2006 | Berner et al. |
| 2006/0264509 | A1 | 11/2006 | Fraser et al. |
| 2007/0184104 | A1 | 8/2007 | Berner et al. |
| 2009/0017121 | A1 | 1/2009 | Berner et al. |
| 2009/0176882 | A1 | 7/2009 | Berner et al. |
| 2010/0247610 | A1 | 9/2010 | Berner et al. |
| 2011/0218246 | A1 | 9/2011 | Berner et al. |
| 2012/0027823 | A1 | 2/2012 | Berner et al. |
| 2012/0064129 | A1 | 3/2012 | Berner et al. |
| 2012/0064168 | A1 | 3/2012 | Berner et al. |
| 2012/0128735 | A1 | 5/2012 | Berner et al. |

FOREIGN PATENT DOCUMENTS

| | | | |
|---|---|---|---|
| WO | WO 98/56360 | A1 | 12/1998 |
| WO | WO 99/12537 | A1 | 3/1999 |
| WO | WO 99/47128 | A1 | 9/1999 |
| WO | WO 00/53225 | A1 | 9/2000 |
| WO | WO 00/59477 | A1 | 10/2000 |
| WO | WO 00/76478 | A1 | 12/2000 |
| WO | WO 01/13894 | A1 | 3/2001 |
| WO | WO 01/37812 | A1 | 5/2001 |
| WO | WO 01/97612 | A1 | 12/2001 |
| WO | WO 01/97782 | A1 | 12/2001 |
| WO | WO 03/002101 | A1 | 1/2003 |
| WO | WO 03/002151 | A1 | 1/2003 |
| WO | WO 03/011255 | A1 | 2/2003 |
| WO | WO 03/035040 | A1 | 5/2003 |

OTHER PUBLICATIONS

Asconape et al., "Myclonus associated with the use of gabapentin", Epilepsia, vol. 41, pp. 479-481(2000).

Ashton et al., "GABA-ergic drugs: exit stage left, enter stage right", Journal of Psychopharmacology, vol. 17, No. 2, pp. 174-178 (2003).

Backonja et al., "Gabapentin for the symptomatic treatment of painful neuropathy in patients with diabetes milletus", JAMA, vol. 280, pp. 1831-1836 (1998).

Bebin et al., "New anticonvulsant drugs: focus on flunarizine, fosphenytoin, midazolam and stiripentol", Drugs, vol. 48, pp. 153-171 (1994).

Benedetti, "Enzyme induction and inhibition by new antiepileptic drugs: a review of human studies", Fund. Clin. Pharmac., vol. 14, pp. 301-319 (2000).

Benetello et al., "Oral gabapentin disposition in patients with epilepsy after a high-protein meal", Epilepsia, vol. 38, No. 10, pp. 1140-1142 (1997).

Ben-Menachem, "New antiepileptic drugs and non-pharmacological treatments", Curr. Opin. Neurol., vol. 13, pp. 165-170 (2000).

Bennett et al., "Gabapentin in the treatment of neurophathic pain", Palliative Med., vol. 18, No. 1, pp. 5-11 (2004).

Bennett et al., "Future directions in the management of pain by intraspinal drug delivery", J. Pain and Symptom Management, vol. 20, No. 2, pp. S44-S50 (2000).

Bernus et al., "Anticonvulsant therapy in aged patients: clinical pharmacokinetic considerations", Drugs & Aging, vol. 10, pp. 278-289 (1997).

Beydoun, "Monotherapy trial of new antiepileptic drugs", Epilepsia, vol. 38, No. 9, pp. S21-S31 (1997).

Bialer, "Comparative pharmacokinetics of the newer antiepilieptic drugs", Clin. Pharmacokinet., vol. 24, pp. 441-452 (1993).

Blum et al., "Pharmacokinetics of gabapentin in subject with various degrees of renal function", Clin. Pharmacol. Ther., vol. 56, pp. 154-159 (1994).

Bourgeois, "Important pharmacokinetic properties of antiepileptic drugs", Epilepsia, vol. 36, pp. 5, pp. S1-S7 (1995).

Bourgeois, "New antiepileptic drugs", Arch. Neurol., vol. 55, pp. 1181-1183 (1998).

Bourgeois, "Pharmacokinetic properties of current antiepileptic drugs: what improvements are needed?", Neurology, vol. 55, No. 3, pp. S11-S16 (2000).

Boyd et al., "Clinical research: effects of age and gender on single-dose pharmacokinetics of gabapentin," Epilepsia, vol. 40, pp. 474-479(1999).

Brown et al., "Cloning and deletion mutagenesis of the $\alpha_2\delta$ calcium channel subunit from porcine cerebral cortex", J. Biol. Chem., vol. 273, pp. 25458-25465 (1998).

Browne, "Long-term efficacy and toxicity of gabapentin", Neurology, vol. 43, pp. A307 (1993).

Bryans et al., "3-substitute GABA analogs with central nervous system activity: A review", Medicinal Research Reviews, vol. 19, No. 2, pp. 149-177 (1999).

Chadwick et al., "Clinical administration of new antiepileptic drugs, an overview of safety and efficacy", Epilepsia, vol. 37, No. 6, pp. S17-S22 (1996).

Chadwick, "An overview of the efficacy and tolerability of new antiepileptic drugs", Epilepsia, vol. 38, No. 1, pp. S59-S62 (1997).

Chadwick, "Gabapentin", Lancet, vol. 343, pp. 89-91 (1994).

Cramer et al., "New antiepileptic drugs: comparison of key clinical trials", Epilepsia, vol. 40, pp. 590-600 (1999).

Curry et al., "Newer antiepileptic drugs: gabapentin, felbamate, topirimate and fosphenytoin", Am. Family Physician, vol. 57, pp. 513-520 (1998).

Davis et al., "Relationship between the rate of appearance of oxyprenolol in the systematic circulation and the location of an oxyprenolol oros 16/260 drug delivery system within the gastrointestinal tract as determined by scintigraphy", Br. J. Clin. Pharmac., vol. 26, pp. 435-443 (1988).

Davis et al., "Transit of pharmaceutical dosage forms through the small intestine", Gut, vol. 27, pp. 886-892 (1986).

Davis et al., "The effect of density on the gastric emptying of single- and multiple-unit dosage forms", Pharmaceutical Research, vol. 3, No. 4, pp. 208-213 (1986).

Devinsky et al., "New antiepileptic drugs for children: felbamate, gabapentin, lamotrigine and vigabatrin", J. Child Neurology, vol. 9, No. 1, pp. S33-S45 (1994).

DOW Chemical U.S.A. Product Information Publication, "Formulating for controlled release with methocel cellulose ethers", Oct. 5, 2007, pp. 1-34.

Dworkin et al., "Advances in neuropathic pain: diagnosis, mechanisms, and treatment recommendations", Archives of Neurology, vol. 60, pp. 1524-1534 (2003).

Eckhardt et al., "Gabapentin enhances the analgesic effect of morphine in healthy volunteers", Anesth. Analges., vol. 91, pp. 185-191 (2000).

Eldon et al., "Lack of effect of gabapentin on the pharmacokinetics of a norethindrone acetate/ethinyl estradiol-containing oral contraceptive", Neurology, vol. 43, pp. A307 (1993).

Elger et al., "New antiepileptic drugs in eliptology", Neuropsychobiol., vol. 38, pp. 145-148 (1998).

Elwes et al., "Clinical pharmacokinetics of newer antiptileptic drugs", Clin. Pharmcokinet., vol. 30, pp. 403-415 (1996).

Emilien et al., "Pharmacological management of epilepsy, mechanism of action, pharmacokinetics drug interactions, and new drug discovery possibilities", Intl. J. Clin. Pharmacol. Ther., vol. 36, pp. 181-194 (1998).

Fara, "Physiological Limitations: Gastric Emptying and Transit of Dosage Forms", *Rate Control in Drug Therapy*, L.F. Prescott, et al., eds., Churchill Livingstone, New York, (1985).

Feely, "Fortnightly review: drug treatment of epilepsy", BMJ, vol. 318, pp. 106-109 (1999).

Ferrier, "Lamotrigine and gabapentin: alternatives in the treatment of bipolar disorder", Neuropsychobiol., vol. 38, pp. 192-197 (1998).

Fischer et al., "Lack of serious toxicity following gabapentin overdose", Neurology, vol. 44, pp. 982-983 (1994).

Fix, "Oral drug delivery, small intestine and colon", *Controlled Delivery*, Mathiowitz, Ed., Wiley & Sons, Inc., pp. 699-700 (1999).

Freeman et al., "Mood stabilizer combinations: a review of safety and efficacy", Am. J. Psychiatry, vol. 155, pp. 12-21 (1998).

Fromm, "Gabapentin: discussion", Epilepsia, vol. 25, No. 5, pp. S77-S90 (1994).

Genton, "When antiepileptic drugs aggravate epilepsy," Brain Dev., vol. 22, pp. 75-80 (2000).

Ghaemi et al., "Gabapentin treatment of the non-refractory bipolar spectrum: an open case series," J. Affective Disorders, vol. 65, pp. 167-171 (2001).

Gidal et al., "Gabapentin absorption: effect of mixing with foods of varying macronutrient composition", Ann. Pharmacother., vol. 32, pp. 405-409 (1998).

Goa et al., "Gabapentin: a review of its pharmacological properties and clinical potential in epilepsy", Drugs, vol. 46, No. 3, pp. 409-427 (1993).

Gram, "Pharmacokinetics of new antiepileptic drugs", Epilepsia, vol. 37, No. 6, pp. S12-S16 (1996).

Grundy and Foster, "The nifedipine Gastrointestinal Therapeutic System (GITS), Evaluation of Pharmaceutical, Pharmacokinetic and Pharmacological Properties", Clin. Pharmacokinet., vol. 26, pp. 435-443 (1988).

Guberman, "Monotherapy or polytherapy for epilepsy", Canadian J. Neurol. Sci., vol. 25, pp. S3-S8 (1998).

Gusler et al., "Pharmacokinetics of metformin gastric-retentive tablets in healthy volunteers", J. Clin. Pharmacol., vol. 41, No. 6, pp. 655-661 (2001).

Guttuso, Jr. et al., "Gabapentins effects on hot flashes in postmenopausal women: a randomized controlled trial", Am. College of Obstetricians and Gynecologists, vol. 101, No. 2, pp. 337-345 (2003).

Handforth, "Efficacy and tolerance of long-term, high-dose gabapentin: additional observations", Epilepsia, vol. 25, pp. 1032-1037 (1994).

Hansen, "Treatment of chronic pain with antiepileptic drugs: a new era", Southern Med. J., vol. 92, pp. 642-649 (1999).

Hou et al., "Gastric retentive dosage forms: a review", Crit. Rev. Ther. Drug Carrier Syst., vol. 20, No. 6, pp. 461-497 (2003).

Irving et al., "Efficacy and safety of extended-release gabapentin for the treatment of postherpetic neuralgia", Abstract and poster presented at the 9th Int. Conf. On the Mechanisms and Treatment of Neuropathic Pain (2006).

Johnston, "GABA agonists as targets for drug development", Clin. Exp. Pharmacol. Physiol., vol. 19, pp. 73-78 (1992).

Kalviainen et al., "A double-blind study of gabapentin in treatment of partial seizures", Epilepsia, vol. 30, pp. 661 (1989).

Kelly, "Gabapentin—antiepileptic mechanism of action", Neuropsychology, vol. 38, pp. 139-144 (1998).

Khurana et al., "Efficacy of gabapentin therapy in children with refractory partial seizures", J. Pediatrics, vol. 128, pp. 829-833 (1996).

Kushnir et al., "Analysis of gabapentin in serum and plasma by solid-phase extraction and gas chromatography—mass spectrometry for therapeutic drug monitoring", J. Anal. Toxicol., vol. 23, pp. 1-6 (1999).

Laird et al., "Use of gabapentin in the treatment of neuropathic pain", Ann. Pharmacotherapy, vol. 34, pp. 802-807 (2000).

Leiderman et al., "Gabapentin as add-on therapy for refractory partial epilepsy: results of five placebo-controlled trials", Epilepsia, vol. 35, No. 5, pp. S74-S76 (1994).

Letterman et al., "Gabapentin: a review of published experience in the treatment of bipolar disorder and other psychiatric conditions", Pharmacother., vol. 19, pp. 565-572 (1999).

Loiseau, "Treatment of concomitant illnesses in patients receiving anticonvulsants: drug interactions of clinical significance", Drug Safety, vol. 19, pp. 495-510 (1998).

MacDonald et al., "Antiepileptic drug mechanisms of action", Epilepsia, vol. 34, No. 5, pp. S1-S8 (1993).

Magnus, "Nonepileptic uses of gabapentin", Epilepsia, vol. 40, No. 6, pp. S66-S72 (1999).

Mancardi et al., "Gapapentin is effective in treating nocturnal painful tonic spasms in multiple sclerosis", Neurology, vol. 52, No. 2, pp. A134 (1999).

Mao et al., "Gabapentin in pain management", Anaesth. Analges., vol. 91, pp. 680-687 (2000).

Mathew et al., "Efficacy of gabapentin in migraine prophylaxis", Headache, vol. 41, pp. 119-128 (2001).

Mattson, "Antiepileptic drug monitoring: a reappraisal", Epilepsia, vol. 36, No. 5, pp. S22-S29 (1995).

Maurer et al., "Intestinal absorption of gabapentin in rats", Arnzeim-Forsch/Drug Res., vol. 41, pp. 104-106 (1991).

McLean, "Gabapentin", Epilepsia, vol. 36, No. 2, pp. S73-S86 (1995).

Meldrum, "Update on the mechanism of action of antiepileptic drugs", Epilepsia, vol. 37, Bo. 6, pp. S4-S11 (1996).

Miles et al., "Differentiating possible transport mechanisms for the intestinal absorption of gabapentin", Pharmac. Res., vol. 11, No. 1, pp. S365 (1994).

Miles et al., "Variables affecting the intestinal absorption of water soluble and insoluble antiepileptic agents", Pharmac. Res., vol. 10, No. 10, pp. S223 (1993).

Morrell, "The new antiepileptic drugs and women: fertility, reproductive health, pregnancy and fetal outcome", Epilepsia, vol. 37, No. 6, pp. S34-S44 (1996).

Morrell, "Epilepsy in women: the science of why it is special", Neurology, vol. 53, No. 1, pp. S42- S48 (1999).

Morris, "Gabapentin", Epilepsia, vol. 40, No. 5, pp. S63-S70 (1999).

Muscas et al., "Conversion From Thrice Daily to Twice Daily Administration of Gabapentin (GBP) in Partial Epilepsy: Analysis of Clinical Efficacy and Plasma Levels", Seizure, vol. 9, No. 1, pp. 47-50 (2000).

NDA 20-235 (U.S. Food and Drug Administration application No. 020235), retrieved Dec. 22, 1993.

NDA 20-235 obtained via Freedom of Information Act, "Basics Pharmacokinetics Bioavailability"—optimal absorption, dose proportionality, and sustained release formulation (study #877-076) and "general comments to the medical reviewer.", retrieved Dec. 22, 1993.

NDA 20-882 (U.S. Food and Drug Administration application No. 020882), retrieved Nov. 18, 2010.

NDA 21-129 (U.S. Food and Drug Administration application No. 021129), retrieved Nov. 18, 2010.

Pande et al., "Placebo-controlled study of gabapentin treatment of panic disorder," J. Clin. Psychopharmacol., vol. 20, pp. 467-471 (2000).

Pande et al., "Treatment of social phobia with gabapentin: a placebo-controlled study", J. Clin. Psychopharmacol., vol. 19, pp. 341-348 (1999).
Parks et al., "Practical therapeutics: drug therapy for epilepsy", Am. Family Physican, vol. 50, pp. 639-648 (1994).
Patsalos et al., "Newer Antiepileptic drugs: towards an improved risk-benefit ratio," Drug Safety, vol. 11, pp. 37-67 (1994).
Perucca et al., "Antiepileptic drugs as a cause of worsening seizures", Epilepsia, vol. 39, pp. 5-17 (1998).
Perucca, "The new generation of antiepileptic drugs: advantages and disadvantages", Br. J. Clin. Psychopharmacol., vol. 42, pp. 531-543 (1996).
Piyapolrungroj et al., "Mucosal uptake of gabapentin (neurontin) vs. pregabalin in the small intestine", Pharm. Res., vol. 18, No. 8, pp. 1126-1130 (2001).
Raby, "Gabapentin therapy for cocaine cravings", Am. J. Psychiatry, vol. 157, pp. 2058-2059 (2000).
Ragucci et al., "Gabapentin-induced hypersensitivity syndrome", Clin. Neuropharmacol., vol. 24, pp. 103-105 (2001).
Richter et al., "Pregabalin or morphine and gabapentin for neuropathic pain", Expert Op. On Pharmacotherapy, vol. 6, No. 14, pp. 2535-2539 (2005).
Riva et al., "Pharmacokinetics interactions between antiepileptic drugs: clinical considerations", Clin. Pharmacokinetics, vol. 31, pp. 470-493 (1996).
Rocci et al., "Food-induced gastric retention and absorption of sustained-release procainamide", Clin. Pharmacol. Ther., vol. 42, pp. 45-49 (1987).
Rosenberg et al., "The effect of gabapentin on neuropathic pain", Clin. J. Pain, vol. 13, pp. 251-255 (1997).
Rowan et al., "intensive monitoring and pharmacokinetics studies of gabapentin in patients with generalized spike-wave discharges", Epilepsia, vol. 30, pp. 661(1989).
Sabers et al., "New anticonvulsants: comparative review of drug interactions and adverse effects", Drugs, vol. 60, pp. 23-33 (2000).
Salinsky et al., "Effects of chronic gabapentin and carbamazepine treatment on EEG, alertness and cognition in healthy volunteers", Epilepsia, vol. 41, No. 7, pp. 151, Abst. #2240 (2000).
Schmidt et al., "The new anticonvulsant drugs: implications for avoidance of adverse effects", Drug Safety, vol. 11, pp. 422-431 (1994).
Shovron et al., "Overview of the safety of newer antiepileptic drugs", Epilepsia, vol. 38, No. 1, pp. S45-S51 (1997).
Sindrup et al., "Efficacy of pharmacological treatments of neuropathic pain: an update and effect related to mechanism of drug action", Pain, vol. 83, pp. 389-400 (1999).
Sirkia et al., "Use of hydrophilic polymers to control drug release from press-coated oxybutynin hydrochloride tablets", S.T.P. Pharma Sciences, vol. 3, No. 6, pp. 453-458 (1993).
Sivenius et al., "Double-blind study of gabapentin in the treatment of partial seizures", Epilepsia, vol. 32, pp. 539-542 (1991).
Solaro et al., "Gabapentin is effective in treating nocturnal painful spasms in multiple sclerosis", Multiple Sclerosis, vol. 6, pp. 192-193 (2000).
Soliman et al., "Gabapentin treatment for cocaine dependence in methadone-maintained opioddependent patients", Drug Alcohol Depend., vol. 60, Supp. 1, Abst. #S208 (2000).
Stevenson et al., "Contrasting nutrient effects on the plasma level of an amino acid-like antiepileptic agent from jejunal administration in dogs", J. Pharm. Sci., vol. 86, No. 8, pp. 953-957 (1997).
Stevenson et al., "Colonic Absorption of Antiepileptic Agents", Epilepsia, vol. 38, pp. 63-67 (1997).
Stewart et al., "A saturable transport mechanism in the intestinal absorption of gabapentin in the underlying cause of the lack of proportionality between increasing dose and drug levels in plasma", Pharmac. Res., vol. 10, pp. 276-281 (1993).
Thomson et al., "Pharmacokinetics optimization of anticonvulsant therapy", Clin. Pharmacokinet., vol. 23, pp. 216-230 (1992).
Tomson, "Therapeutic monitoring of the new antiepileptic drugs", Eur. J. Clin. Pharmacol., vol. 55, pp. 697-705 (2000).
Upton, "Mechanisms of action of new antiepileptic Drugs: rational design and serendipitous findings", Tips, vol. 15, pp. 456-463 (1994).
Vollmer, "Pharmacokinetics and metabolism of gabapentin in rat, dog and man", Arnzeim-Forsch/Drug Res., vol. 36, pp. 830-839 (1986).
Wang et al., "The simultaneous estimation of the influx and efflux blood-brain barrier permeabilities of gabapentin using a microdialysis-pharmacokinetic approach", Pharmac. Res., vol. 13, pp. 398-403 (1996).
Welling and Barbhajya, "Influence of Food and Fluid vol. On Chlorothiazide Bioavailability: Comparison of Plasma and Urinary Excretion Methods", J. Pharm. Sci., vol. 71, pp. 32-35(1982).
Wesche et al., "A pharmacokinetic comparison of pregabalin and gabapentin", J. Pain, vol. 6, No. 3, (2005) abstract only.
Wheeler, "Gabapentin", Current Opinion in Investigational Drugs, vol. 3, No. 3, pp. 470-477 (2002).
White, "Comparative anticonvulsant and mechanistic profile of the established and newer antiepileptic drugs", Epilepsia, vol. 40, No. 5, pp. S2-S10 (1999).
Wilding et al., "Relationship Between Systemic Drug Absorption and Gastrointestinal Transit After the Simultaneous Oral Administration of Carbamazepine as a Controlled-Release System and as a Suspension of $^{15}$N-Labelled Drug to Healthy Volunteers", Br. J. Clin Pharmac., vol. 32, pp. 573-579 (1991).
Wolf et al., "Gabapentin toxicity in children manifesting as behavioral changes," Epilepsia, vol. 36, pp. 1203-1205 (1996).
Wong et al., "Adverse reactions to new anticonvulsant drugs", Drug Safety, vol. 239, pp. 35-56 (2000).
Wong et al., "Clinical research: the long-term use of gabapentin, lamotrigine and vigabatrin in patients with chronic epilepsy", Epilepsia, vol. 40, pp. 1439-1445 (1999).
Wong et al., "Disposition of gabapentin in anuric subjects on hemodialysis", J. Clin. Pharmacol., vol. 35, pp. 622-626 (1995).
Zylicz, "Painful gynecomastia: an unusual toxicity of gabapentin", Letters, vol. 20, pp. 2-3 (2000).
Adelman and Adelman, "Current options for the prevention and treatment of migrane", Clin. Ther., vol. 23, No. 6, pp. 772-788 (2001).
Apicella et al., "Poly(ethylene oxide) (PEO) and different molecular weight PEO blends monolithic devices for drug release", Biomaterials, vol. 14, No. 2, pp. 83-90 (1993).
Babu et al., "In vitro and in vivo studies of sustained-release floating dosage forms containing slbutamol sulfate", Pharnazue, vol. 45, pp. 268-270 (1990).
Backonja et al., "Gabapentin for the treatment of painful neuropathy in patients with diabetes mellitus, A randomized controlled study", JAMA, vol. 280, No. 21, pp. 1831-1836 (1998).
Bazil and Bazil, "Recent advances in the pharmacotherapy of epilepsy", Clin. Ther., vol. 19, Issue 3, pp. 369-382 (1997).
Bolger et al., "Simulation of the nonlinear does dependence for substrates of influx and efflux transporters in the human intestine", The AAPS Journal, vol. 11, No. 2, pp. 353-363 (2009).
"Drug delivery to the gastrointestinal tract", Hardy et al., ed., *Ellis Horwood books in biological sciences, Series in phamaceutical technology*, Ellis Horwood limited, Halstad Press: a division of John Wiley & Sons, New York, NY, USA, Chapter 3, pp. 37-48 (1989).
Di Trapani et al., "Gabapentin in the prophyiaxis of migrane: a double-blind ramdomized placebo-controlled study", Clin. Ter., vol. 151, No. 3, pp. 145-148 (2000) Abstract Only.
Edgren et al., "Contrilled release technology, pharmaceutical", *Kirk-Othmer encyclipedia of Chemical Technology*, John Wiley & Sons, Inc., Online ISBN: 9780471238966, doi: 10.1002/0471238961, 24 pgs. (2000).
Ford et al., "Importance of drug type, tablet shape and added diluents on drug release kinetics from hydroxypropylmethylcellulose matrix tablets", Int'l. J. Pharmaceutics, vol. 40, pp. 223-234 (1987).
Hunt et al., "relation between the chain length of fatty acids and the slowing of gastric emptying", J. Physiol., vol. 194, pp. 327-336 (1968).
Khosla and Davis, "The effect of tablet size on the gastric emptying of non-disintergrating tablets", Int. J. Pharm., vol. 62, pp. R9-R11 (1990).
Kim, "Drug release from compressed hydrophilic POLYOX-WSR tablets", J. Pharmaceutical Sci., vol. 84, No. 3, pp. 303-306 (1995).

Lal et al., "Clinical pharmacokinetic drug interaction studies of gabapentin enacarbil, novel transported prodrug of gabapentin, with naproxed and cimetidine", Br. J. Clin. Pharmacol., vol. 69, No. 5, pp. 498-507 (2010).

Mathew et al., "Efficacy of gabapentin in migrane prophylaxis", Headache, vol. 41, No. 2, pp. 119-128 (2001).

McLean, "Gabapentin: chemistry, absorption, distribution, and excretion", *Antiepileptic Drugs, 4th Edition*, Levy Mattson, and Meldrum, eds., Raven Press, Ltd., New York, NY, USA, pp. 843-849 (1995).

Papadimitriou et al., "Swelling studies on mixtures of two hydrophilic excipients", S.T.P. Pharma Sciences, vol. 3, No. 3, pp. 232-236 (1993).

Park "Enzyme-digestible swelling hydrogels swelling hydrogels as platforms for long-term oral drug delivery: synthesis and characterization", Biomaterials, vol. 9, No. 5, pp. 435-441 (1988).

"Pharmaceutical Dosage Forms" *Durgin and Hanan's Pharmacy for Technicians, 4th Edition*, Durgin and Hanan, eds., Delmar Cengage Learning, Clifton Park, NY, USA, Chapter 12, pp. 198-228 (2008).

*Remington: The science and practive of pharmacy, 19th Edition*, Gennaro, ed., Mack Publishing Company, Easton, Pennsylvania, USA, Chapter 92, pp. 1628-1629 (1995).

Rowbotham et al., "Gabapentin for the treatment of postherpetic neuralgia, A randomized control study", JAMA, vol. 280, No. 21, pp. 1837-1842 (1998).

Shalaby et al., "Invitro and in vivo studies of enzyme-digestible hydrogels for oral drug delivery", J. Controlled Release, vol. 19, pp. 131-144 (1992).

Shojaei and Berner, "Gastric retentive dosage forms", *Design of Contrilled Release Drug Delivery Systems*, Li and Jasti, ed., McGraw Hill, New York, NY, USA, pp. 173-201 (2006).

SIST et al., "Experience with gabapentin for neuropathic pain in the head and neck: report of ten cases", Regional Ansdthesia, vol. 22, No. 5, pp. 473-478 (1997).

"Spevific delivery to the gastrointestinal tract", *Polymeric Site-Specific Pharmacotherapy*, Domb, ed., John Wiley & Sons, Ltd., Chichester, West Sussex, England, pp. 282-283 (1994).

*The Pill Book*, 8th Edition, Silverman, ed., Bantam Books, New York, pp. B-C, J-K (1998).

Timmermans et al., "The cutoff size for gastric emptying of dosage forms", J. Pharm. Sci., vol. 82, No. 8, pp. 854 (1993).

Timmermans and Moes, "Factors controlling the buiyancy and gastric retention capabilities of floating matrix capsules: new data for reconsidering the controversy", J. Pharm. Sci., vol. 83, No. 1, pp. 18-24 (1994).

Beydoun et al., "Gabapentin: pharmacokinetics, efficacy, and safety", Clinical Neuropharmacoloqy, vol. 18, No. 6, pp. 469-481 (1995).

Collins et al., "Extended release formulations of anticonvulsant medications", CNS Drugs, vol. 14, No. 3, pp. 203-212 (2000).

Deshpande et al., "Development of novel contrilled-release system for gastric retention" Pharm. Res., vol. 14, No. 6, pp. 815-819 (1997).

Feely and Davis, "Correlation of phenylpropanolamine bioavailability with gastrointestinal transit by scintigraphic monitoring of 111ln-labeled hydroxypropylmethylcellulose matrices", Pharmaceutical Research, vol. 6, No. 4, pp. 274-278 (1989).

Gidal et al., "Gabapentin bioavailavility: effect of dose and frequency of administration in adult patients with epilepsy", Epilepsy Research, vol. 31, No. 2, pp. 91-99 (1998).

Hwang, "Gastric retentive drug-delivery systems", Critical Reviews in Therapeutic Drug Carrier Systems, vol. 15, No. 3, pp. 243-284 (1998).

Kriel et al., "Failure of absorption of gabapentin after rectal administration", Epolepsia, vol. 38, No. 11, pp. 1242-1244 (1997) Abstract only.

Lee et al., "Oral mucisa contrilled delivery of LHRH by bilayer mucoadhesive polymer systems", J. Contr. Rel., vol. 19, pp. 251-261 (1995).

Leppik, "Antiepileptic drugs in development: prospects for the near future", Epilepsia, vol. 35, Suppl. 4, pp. S29-S40 (1994).

*Polyox Water-Soluble Resins NF in Pharmacuetical Applications*, "An introduction to POLYOX water soluble resins", The Dow Chemical Company, Brochure, 12 pgs. (2004).

Rao et al., "Influence of milecular size and water solubility of the solute on its release from swelling and erosion controlled polymeric matrices", J. Conrolled Release, vol. 12, Issue 2, pp. 133-141 (1990).

Timmins et al., "Optimization and characterization of a pH-independent extended-release hydrophilic matrix tablet",. Pharmaceutical Development & Technology, vol. 2, No. 1, pp. 25-31 (1997).

Vollmer et al., "Summart of neurontin (gabapentin) clinical pharmacokinetics", Epilepsia, vol. 33, Suppl. 3, pp. 77 (1992).

Welling, "Interactions affecting drug absorption", Pharmacokinet., vol. 9, No. 5, pp. 404-434 (1984).

\* cited by examiner

GASTRIC RETAINED GABAPENTIN DOSAGE FORM

PRIORITY

This application is a continuation of U.S. application Ser. No. 12/749,101, filed Mar. 29, 2010, now allowed, which is a continuation of U.S. application Ser. No. 12/239,591, filed Sep. 26, 2008, now U.S. Pat. No. 7,731,989, which is a continuation of U.S. Ser. No. 10/280,309 filed Oct. 25, 2002, now U.S. Pat. No. 7,438,927, which claims priority to U.S. Provisional Application Ser. No. 60/335,248, filed on Oct. 25, 2001, all of which are incorporated herein by reference in their entirety.

BACKGROUND OF THE INVENTION

1. Technical Field

The present invention relates to the use of gabapentin in a gastric retained dosage form. More specifically, the invention relates to the use of such dosage form to treat epilepsy and other disease states.

2. Background

Gabapentin (1-(aminomethy)cyclohexaneacetic acid) is an anti-epileptic drug that is currently available in 100 mg, 300 mg and 400 mg hard shell capsule as well as 600 mg and 800 mg tablet dosage forms, with recommended dosing of 900 mg to 1800 mg total daily dose in three divided dosages. The oral bioavailability is dose-dependent, with approximately 60% bioavailability for a dose in the range of 300-400 mg, but with only 35% bioavailability for a dose of 1600 mg (Bourgeois, *Epilepsia* 36 (Suppl. 5):S1-S7 (1995); Gram, *Epilepsia* 37 (Suppl. 6):S12-S16 (1996)). The decrease in bioavailability with dose has been attributed to carrier-mediated absorption (Stewart, et al., *Pharmaceutical Research* 10(2):276-281 (1993).

In early work with rats, Vollmer, et al., *Arzneim-Forsch/Drug Research* 36(I, Nr. 5):781-892 (1986) found that the absorption site for gabapentin was the duodenum. The absorption of gabapentin occurs relatively slowly with the peak plasma concentration occurring approximately 2-6 hours after dosing (Bourgeois, supra). The elimination of gabapentin is exclusively through renal pathways (Chadwick; *The Lancet* 343:89-91 (1994); Vollmer, supra; Thomson, et al., *Clin. Pharmacokinet.* 23(3):216-230 (1992); and Riva, et al., *Clin. Pharmacokinet.* 31(6):470-493 (1996)) with reported half-lives of 5-7 hours (Chadwick, supra) and 6-7 hours (Gram, supra).

A once- or twice-daily dosage form of gabapentin would be expected to improve compliance and therefore a controlled release dosage form has some distinct advantages over the conventional immediate release formulations. In addition, a controlled release dosage form would lower the maximum plasma concentration, and this may result in reduced side effects. Since gabapentin is absorbed high in the gastrointestinal tract, by means of a saturable transport mechanism, a gastric retained dosage form is particularly beneficial for delivery of gabapentin since the dosage form would be able to keep the drug in the region of absorption and show improved bioavailability by virtue of the slower release rate that avoids saturation of the carrier mediated transport of conventional dosages.

SUMMARY OF THE INVENTION

One aspect of the invention relates to a method of treating epilepsy comprising administering a therapeutically effective amount of gabapentin or a pharmaceutically acceptable salt thereof, in a gastric retained dosage form to a mammal in need of such treatment.

Yet another aspect of the invention relates to a method of treating neuropathic pain comprising administering a therapeutically effective amount of gabapentin or a pharmaceutically acceptable salt thereof, in a gastric retained dosage form to a mammal in need of such treatment.

Still another aspect of the invention relates to an improved method of administering a therapeutically effective amount of gabapentin to a patient in need thereof, the improvement comprising administering gabapentin or a pharmaceutically acceptable salt thereof, in a gastric retained dosage form.

DESCRIPTION OF THE INVENTION

Figure 1:
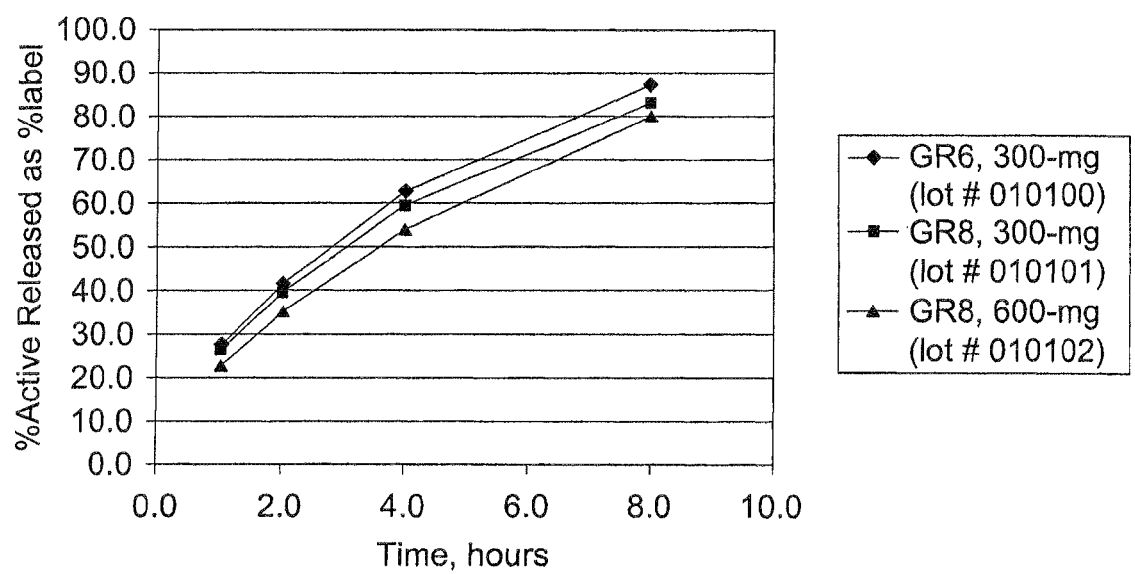
FIG. 1 illustrates the dissolution profiles for three GR™ formulations.

The invention relates to a method of treating a disease state, such as epilepsy, by administering gabapentin in a once- or twice-daily gastric retained dosage form. The gastric retained dosage form is particularly beneficial for delivery of gabapentin due to its prolonged transit in the upper gastrointestinal tract, which allows the drug to be absorbed adequately in the preferred region of absorption. In addition, a gastric retained dosage form increases the $t_{max}$ and allows for a smoother, more prolonged anti-spasmolytic effect. This dosage form also lowers the $C_{max}$ and may result in reduced incidence and/or severity of CNS side effects of the drug, such as somnolence, ataxia, fatigue and dizziness.

Method of Treatment

The instant invention is a method of treating a disease state comprising administering a therapeutically effective amount of gabapentin, or a pharmaceutically acceptable salt thereof, once- or twice-daily in a gastric retained dosage form to a mammal in need of such treatment. As used herein, the term "treating" covers treating the specified disease in a mammal, particularly a, and includes:

(i) preventing the disease from occurring in a subject which may be predisposed to the disease but has not yet been diagnosed as having it;

(ii) inhibiting the disease, i.e. arresting its development; or (iii) relieving the disease, i.e. causing regression of the disease.

One embodiment of the invention relates to an improved method of administering a therapeutically effective amount of gabapentin to a patient in need thereof, the improvement comprising administering gabapentin or a pharmaceutically acceptable salt thereof, in a gastric retained dosage form.

Other embodiments of the invention relate to methods of treating specific disease states comprising administering a therapeutically effective amount of gabapentin or a pharmaceutically acceptable salt thereof, in a gastric retained dosage form to a mammal in need of such treatment. Such methods find utility in treating numerous disease states that are currently being treated with conventional immediate release formulations of gabapentin and include, by way of illustration and not limitation, epilepsy; neuropathic pain; psychiatric disorders such as bipolar disorder and panic disorder; movement disorders such as restless leg syndrome, periodic movement disorder of sleep, essential tremor and acquired nystagmus; and prophylaxis of migraine headaches.

The invention also contemplates administering one or more additional therapeutic agents with the gabapentin treatment. The selection of these additional therapeutic agents will depend upon the specific disease state being treated, and are described in detail below.

Active Ingredient

The active ingredient in the method of the invention is gabapentin. Gabapentin is preferably used in the free amphoteric form. Pharmaceutically acceptable salt forms that retain the biological effectiveness and properties of gabapentin and are not biologically or otherwise undesirable can also be used and may show superior bioavailability. As used herein, the term "gabapentin" is intended to include the agent itself, as well as its pharmaceutically acceptable salts.

Pharmaceutically acceptable salts may be amphoteric and may be present in the form of internal salts. Gabapentin may form acid addition salts and salts with bases. Exemplary acids that can be used to form such salts include, by way of example and not limitation, mineral acids such as hydrochloric, hydrobromic, sulfuric or phosphoric acid or organic acids such as organic sulfonic acids and organic carboxylic acids. Salts formed with inorganic bases include, for example, the sodium, potassium, lithium, ammonium, calcium, and magnesium salts. Salts derived from organic bases include, for example, the salts of primary, secondary and tertiary amines, substituted amines including naturally-occurring substituted amines, and cyclic amines, including isopropylamine, trimethylamine, diethylamine, triethylamine, tripropylamine, ethanolamine, 2-dimethyl aminoethanol, tromethamine, lysine, arginine, histidine, caffeine, procaine, hydrabamine, choline, betaine, ethylenediamine, glucosamine, N-alkylglucamines, theobromine, purines, piperazine, piperidine, N-ethylpiperidine, fumarate, maleate, succinate, acetate and oxalate.

Additional Therapeutic Agents

The methods of the invention also contemplate the addition of one or more therapeutic agents with the gabapentin treatment.

For those embodiments of the invention where the gabapentin gastric retained dosage form is administered to treat epilepsy, such additional therapeutic agents can be other antiepileptics or anticonvulsants, which include, by way of illustration and not limitation, hydantoins, iminostilbenes, valproates, phenyltriazines, barbiturates, deoxybarbiturates, benzodiazepines and carbamates. Such additional agents are preferably hydantoins, iminostilbenes, valproates or phenyltriazines.

The following examples of compounds within each of these classes is intended to be illustrative and not limiting in any manner. Examples of suitable hydantoin anticonvulsants include ethotoin, fosphenyloin, mephenyloin, and, preferably, phenyloin. An examples of a suitable iminostilbene is carbamazepine. Examples of suitable valproates include valprioic acid and sodium valproate. An exemplary suitable phenyltriazine is lamotrigene. A suitable barbiturate is phenobarbital and an exemplary deoxybarbiturate is primidone. An example of a suitable benzodiazepine is clorazepate. A suitable carbamate is felbamate.

For those embodiments of the invention where the gabapentin gastric retained dosage form is administered to treat neuropathic pain, such additional therapeutic agents can be selected from the group consisting of other anticonvulsants, tricyclic antidepressants, levadopa, and opioids.

The following examples of compounds within each of these classes is intended to be illustrative and not limiting in any manner. Examples of suitable anticonvulsants include carbamazepine, phenyloin and lamotrigine. Suitable tricyclic antidepressants include amitriptyline, imipramine, clomipramine and desipramine. Examples of suitable opioids include oxycodone and tramadol.

For those embodiments of the invention where the gabapentin gastric retained dosage form is administered to treat psychiatric disorders, such additional therapeutic agents can be selected from the group consisting of lithium, carbamazepine, valproate, trifluoperazine, clonazepam, risperidone, lorazepam, venlafaxine, clozapine, olanzapine, benzodiazepines, neuroleptics, tricyclic antidepressants, selective serontin reuptake inhibitor (SSRI's), buprupion, and nefadone.

For those embodiments of the invention where the gabapentin gastric retained dosage form is administered to treat bipolar disorder, such additional therapeutic agents can be selected from the group consisting of lithium, carbamazepine, valproate, trifluoperazine, clonazepam, risperidone, lorazepam, venlafaxine, clozapine, olanzapine, benzodiazepines, and neuroleptics.

For those embodiments of the invention where the gabapentin gastric retained dosage form is administered to treat depression, such additional therapeutic agents can be selected from the group consisting of tri-cyclic anti-depressants, SSRI's, bupropion, venlaxatine, and nefadone.

For those embodiments of the invention where the gabapentin gastric retained dosage form is administered to treat manic disorders, such additional therapeutic agents can be selected from the group consisting of diazepam, and oxazepam.

For those embodiments of the invention where the gabapentin gastric retained dosage form is administered to treat movement disorders, such additional therapeutic agents can be selected from the group consisting of benzodiazepines, dopaminergic agents, and opiates, particularly levodopa/carbidopa and clonazepam.

For those embodiments of the invention where the gabapentin gastric retained dosage form is administered for prophylactic treatment of migraine headaches, such additional therapeutic agents can be selected from the group consisting of tricyclic antidepressants (amitriptyline, doxepin, imipramine, maprotiline, protriptyline, desipramine), SSRI (fluoxetine), triptine (sumatriptan, etc.), and ergotamine.

Dosage

In general, the term "therapeutically effective amount" refers to that amount which is sufficient to effect treatment, when administered to a mammal in need of such treatment. The therapeutically effective amount will vary depending on the subject being treated, the severity of the disease state and the manner of administration, and may be determined routinely by one of ordinary skill in the art.

In particular, for use in the treatment of epilepsy or neuropathic pain with a gastric retained dosage form, gabapentin may be used at doses appropriate for treating epilepsy or neuropathic pain with immediate release dosage forms. However, the gastric retained dosage form is designed to provide for bioavailability of gabapentin at a level greater than or equal to 80% ($\geq 80\%$) relative to an equal dose of an immediate release dosage form. Typically, the method of the invention will involve administering gabapentin on a once- or twice-daily basis for as long as the condition persists.

An effective dosage of gabapentin for the treatment of epilepsy is typically in the range of about 300-3600 mg/day, typically about 900-2400 mg/day, more typically about 900-1800 mg/day.

An effective dosage of gabapentin for the treatment of neuropathic pain is typically in the range of about 100-4800 mg/day, typically about 300-3600 mg/day, more typically about 900-2400 mg/day.

An effective dosage of gabapentin for the treatment of psychiatric disorders is typically in the range of about 100-4800 mg/day, more typically about 900-3600 mg/day.

An effective dosage of gabapentin for the treatment of movement disorders is typically in the range of about 100-4000 mg/day, typically about 200-2700 mg/day, more typically about 500-2700 mg/day.

An effective dosage of gabapentin for the prophylactic treatment of migraine headaches is typically in the range of about 200-4000 mg/day, typically about 500-3600 g/day, more typically about 900-2400 mg/day.

Dosage Regimen

The methods of the invention provide a once- or twice-daily dose of the gabapentin gastric retained dosage form. The dosage can be administered at any time, but it is preferred that the dosage is administered at the same approximate time each day and in approximately 12 hour intervals for the duration of treatment. In addition, it is preferred that the gastric retained dosage form be taken with food, for example with the morning or evening meals.

Accordingly, in one embodiment of the invention, gabapentin is administered once-daily, for example, in the morning (e.g., upon rising or with the morning meal) or in the evening (e.g., with the evening meal or near bedtime).

In another embodiment of the invention, gabapentin is administered twice-daily, for example, with the first dose being in the morning (e.g., upon rising or with the morning meal) and the second dose being in the evening (e.g., with the evening meal or near bedtime).

In another aspect of the invention, the method of administering a therapeutically effective amount of gabapentin in a gastric retained dosage form further includes administering one or more additional therapeutic agents.

The additional therapeutic agents can be administered at the same time or at a different time than the administration of gabapentin, and will depend upon the nature of the disease being treated as well as the agent itself. For example, when the additional agent is another anti-epileptic, a twice-daily dose is sufficient and it may be administered at the same time or at a different time than gabapentin. For purposes of facilitating patient compliance, administration of any of the aforementioned additional agents at the same time is preferred.

Dosage Form

There are several drug delivery systems that are suitable for use in delivering gabapentin in the method of the invention as they are particularly tailored to be gastric-retained dosages, such as the swellable bilayer described by Franz, et al, U.S. Pat. No. 5,232,704; the multi-layer tablet with a band described by Wong, et al., U.S. Pat. No. 6,120,803; the membrane sac and gas generating agent described in Sinnreich, U.S. Pat. No. 4,996,058; the swellable, hydrophilic polymer system described in Shell, et al., U.S. Pat. No. 5,972,389 and Shell, et al., WO 9855107; all of which are incorporated herein by reference.

Of particular interest are gastric retained dosage forms that contain hydrophilic polymers that swell to a size such that the dosage form is retained in the fed mode. For example, the gastric retained dosage form can contain polymers with a high swelling capacity such as polyethylene oxide, hydroxyethylcellulose and hydroxypropylmethylcellulose. The polymers are preferably of a moderate to high molecular weight ($4 \times 10^3$ to greater that $10^7$) to enhance swelling and provide control of the release of gabapentin. In one embodiment of the invention, a hydroxypropylmethylcellulose polymer of such molecular weight is utilized so that the viscosity of a 1% aqueous solution is about 4000 cps to greater than 100,000 cps. An example of suitable polyethylene oxide polymers are those having molecular weights (viscosity average) on the order of 2-7 million. A typical dosage form should swell to approximately 115% of its original volume within one hour after administration, and at a later time should swell to a volume that is 130% or more of the original volume. Fillers, binders, lubricants and other additives may also be included in the gastric retained dosage form, such as are well known to those of skill in the art.

A typical dosage form would provide for a drug delivery profile such that gabapentin both on an in vivo and in vitro basis, is delivered for at least 5 hours, and typically over a time period of about 8-10 hours. In order to provide for sustained delivery, it is preferable that at least 40 wt % of gabapentin is retained in the dosage form after 1 hour, i.e., no more than 60 wt % of the drug is administered in the first hour. In addition, it may be desired to utilize a dosage form that provides for substantially all of the gabapentin to be delivered over the intended duration, which is typically about 6-12 hours, where substantially all is taken to mean at least about 85 wt % of the gabapentin is administered.

In one embodiment of the invention, the gastric retained dosage form of gabapentin is a capsule dosage form that allows for the extended release of gabapentin in the stomach and comprises: (a) at least one component that expands on contact with gastric juice and contains an agent capable of releasing carbon dioxide or nitrogen, gabapentin or a pharmaceutically acceptable salt thereof; (b) at least one hydrophilic membrane in the form of a sachet which contains component (a), expands by inflation, floats on the aqueous phase in the stomach and is permeable to gastric juice and; (c) capsule dosage form which contains components (a) and (b) and which disintegrates without delay in the stomach under the action of gastric juice. Component (a) may also contain a pharmaceutically acceptable hydrophilic swelling agent such as lower alkyl ethers of cellulose, starches, water-soluble aliphatic or cyclic poly-N-vinylamides, polyvinyl alcohols, polyacrylates, polymethacrylates, polyethylene glycols and mixtures thereof, as well as other materials used in the manufacture of pharmaceutical dosage forms. Further details regarding an example of this type of dosage form can be found in Sinnreich, U.S. Pat. No. 4,996,058.

In another embodiment of the invention, the gastric retained dosage form of gabapentin is an extended release oral drug dosage form for releasing gabapentin into the stomach, duodenum and small intestine of a patient, and comprises: a single or a plurality of solid particles consisting of gabapentin or a pharmaceutically acceptable salt thereof dispersed within a polymer that (i) swells unrestrained dimensionally by imbibing water from gastric fluid to increase the size of the particles to promote gastric retention in the stomach of the patient in which the fed mode has been induced; (ii)

gradually the gabapentin diffuses or the polymer erodes over a time period of hours, where the diffusion or erosion commences upon contact with the gastric fluid; and (iii) releases gabapentin to the stomach, duodenum and small intestine of the patient, as a result of the diffusion or polymeric erosion at a rate corresponding to the time period. Exemplary polymers include polyethylene oxides, alkyl substituted cellulose materials and combinations thereof, for example, high molecular weight polyethylene oxides and high molecular weight or viscosity hydroxypropylmethylcellulose materials. Further details regarding an example of this type of dosage form can be found in Shell, et al., U.S. Pat. No. 5,972,389 and Shell, et al., WO 9855107.

In yet another embodiment, a bi-layer tablet releases gabapentin to the upper gastrointestinal tract from an active containing layer, while the other layer is a swelling or floating layer. Details of this dosage may be found in Franz, et al., U.S. Pat. No. 5,232,704. This dosage form may be surrounded by a band of insoluble material as described by Wong, et al., U.S. Pat. No. 6,120,803.

Another embodiment of the invention uses a gastric retained swellable, sustained-release tablet having a matrix comprised of poly(ethylene oxide) and hydroxypropylmethylcellulose. This dosage form is illustrated in Example 1 and further details may be found in Gusler, et al., "Optimal Polymer Mixtures For Gastric Retentive Tablets," filed on like date herewith and identified as Ser. No. 10/029,134, the disclosure of which is incorporated herein by reference.

For those embodiments of the invention that include further administering additional therapeutic agents simultaneously with gabapentin, these agents can either be administered in the gastric retained dosage form that includes gabapentin or can be administered in a dosage form that is separate from gabapentin. Exemplary dosage forms are described below.

Dosage Form of Additional Agents

For those embodiments of the invention that include further administering one or more additional therapeutic agents, such dosages can be any suitable formulation as are well known in the art. For those additional agents where controlled release is desirable, the agent may be incorporated in the gabapentin gastric retained dosage form or be administered in a separate gastric retained or other controlled release formulation dosage form. For those additional agents where immediate release is desirable, the agent may be incorporated in a coating around the gabapentin gastric retained dosage form or in a separate layer of a bilayer tablet, the agent may be simply enclosed in the capsule of the aforementioned gabapentin gastric retained capsule dosage form, or the agent may be administered in a separate immediate release dosage form.

Typically, dosage forms contain the additional agent (another anti-epileptic or anticonvulsant agent) in combination with one or more pharmaceutically acceptable ingredients. The carrier may be in the form of a solid, semi-solid or liquid diluent, or a capsule. Usually the amount of active agent is about 0.1-95 wt %, more typically about 1-50 wt %. Actual methods of preparing such dosage forms are known, or will be apparent, to those skilled in this art; for example, see *Remington's Pharmaceutical Sciences*, Mack Publishing Company, Easton, Pa., 18th Edition, 1990. The dosage form to be administered will, in any event, contain a quantity of the additional therapeutic agent(s) in an amount effective to alleviate the symptoms of the subject being treated.

In the preparation of pharmaceutical formulations containing the additional therapeutic agent in the form of dosage units for oral administration the agent may be mixed with solid, powdered ingredients, such as lactose, microcrystalline cellulose, maltodextrin, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or pressed into tablets such as chewable and oral disintegrating tablets.

Soft gelatin capsules may be prepared by mixing the active agent and vegetable oil, fat, or other suitable vehicle. Hard gelatin capsules may contain granules of the active agent, alone or in combination with solid powdered ingredients such as lactose, saccharose, sorbitol, mannitol, potato starch, corn starch, amylopectin, cellulose derivatives or gelatin.

Liquid preparations for oral administration may be prepared in the form of syrups or suspensions, e.g. solutions or suspensions containing about 0.2-20 wt % of the active agent and the remainder consisting of sugar or sugar alcohols and a mixture of ethanol, water, glycerol, propylene glycol and polyethylene glycol. If desired, such liquid preparations may contain coloring agents, flavoring agents, saccharin and carboxymethyl cellulose or other thickening agents. Liquid preparations for oral administration may also be prepared in the form of a dry powder to be reconstituted with a suitable solvent prior to use.

When the method of the invention includes administering another anti-epileptic or an anticonvulsant agent, there are numerous commercially available dosage forms that can be administered. In addition, other formulations can be readily designed based upon knowledge in the art, and include the gastric-retained delivery systems described above.

Typical dosage forms of the other anti-epileptics or anticonvulsants suitable for use in the invention include tablets, capsules, oral suspensions and syrup. One of skill in the art can readily prepare one of these exemplary formulations or the other anti-epileptic can be administered by means of one of the numerous commercially available products, examples of which are provided below.

Commercially available hydantoin anticonvulsants include, for example, Peganone® (ethotoin, Abbott); Mesantoin® (mephenyloin, Sandoz); and Dilantin® (phenyloin, Warner-Lambert).

Typical dosage forms of the antineuralgics suitable for use in the invention include tablets, capsules and oral suspensions. One of skill in the art can readily prepare one of these exemplary formulations or the antineuralgic can be administered by means of one of the numerous commercially available products, examples of which are provided below.

Commercially available antineuralgics include, for example, Atretolg® (carbamazepine, Elan).

Although specific examples of suitable anti-epileptic, anticonvulsant agent and antineuralgic formulations are described above, it is understood that the invention is not limited to those examples as there are numerous other formulations that can be used to deliver the other anti-epileptic or anticonvulsant agents.

The general methods of the invention are best understood with reference to the following examples which are intended to enable those skilled in the art to more clearly understand and to practice the present invention. These examples are not intended, nor are they to be construed, as limiting the scope of the invention, but are merely illustrative and representative thereof.

Example 1

Tablets were manufactured using a dry blend process, and hand made on a Carver 'Auto C' Press (Fred Carver, Inc., Indiana). The dry blend process consisted of blending all of the ingredients in a plastic bag, and compressing into a 1000 mg tablet (600 mg gabapentin dose) using a 0.7086"×0.3937" Mod Oval die (Natoli Engineering). The parameters for the operation of the Carver 'Auto C' Press were as follows: 4000 lbs. force, 0 second dwell time (the setting on the Carver Press), and 100% pump speed.

the ingredients in a plastic bag, and compressing into a 600 mg tablet (300 mg gabapentin) using a 0.6299"×0.3937" Mod Oval die (Natoli Engineering). The parameters for the operation of the Carver 'Auto C' Press were as follows: ~2000-2500 lbs. force, 0 second dwell time (the setting on the Carver Press), and 100% pump speed.

| | Formulation Composition (wt %) | | | |
|---|---|---|---|---|
| Sample # | Active | PEO Coagulant | Methocel K100M | M.St. |
| 1 | 60.0 | 39.0 | 0.0 | 1 |
| 2 | 60.0 | 24.3 | 14.7 | 1 |
| 3 | 60.0 | 0.0 | 39.0 | 1 | where:
Active=gabapentin
PEO Coagulant=poly(ethylene oxide), grade PolyOx Coagulant, NF FP grade, manufactured by Union Carbide/Dow Chemical Company
Methocel KI00M=hydroxypropylmethylcellulose, grade Methocel KI00M, premium, manufactured by Dow Chemical Company
M.St.=magnesium stearate, NF, supplied by Spectrum Chemical Company The dissolution was determined in USP apparatus I(40 mesh baskets), 100 rpm, in deionized water. Samples, 5 ml at each time-point, were taken without media replacement at 1, 4 and 8 hours.

The resulting cumulative dissolution profile, based upon a theoretical percent active added to the formulations is presented in tabulated form below:

| | Theoretical (wt %) of Active Released | | |
|---|---|---|---|
| Time (hours) | Sample 1 | Sample 2 | Sample 3 |
| 1 | 15.4 | 14.8 | 18.6 |
| 4 | 39.4 | 37.4 | 43.3 |
| 8 | 61.7 | 57.8 | 64.7 |

Example 2

Tablets were manufactured using a dry blend process, and hand made on a Carver 'Auto C' Press (Fred Carver, Inc., Indiana). The dry blend process consisted of blending all of

| | Formulation Composition (wt %) | | | |
|---|---|---|---|---|
| Sample # | Active | PEO Coagulant | Methocel K15M | M.St. |
| 4 | 50.0 | 24.5 | 24.50 | 1 | where:
Active=gabapentin
PEO Coagulant=poly(ethylene oxide), grade PolyOx Coagulant, NF FP grade, manufactured by Union Carbide/Dow Chemical Company
Methocel K15M=hydroxypropylmethylcellulose, grade Methocel KI5M, premium, manufactured by Dow Chemical Company
M.St.=magnesium stearate, NF, supplied by Spectrum Chemical Company The dissolution was determined in USP apparatus I (40 mesh baskets), 100 rpm, in deionized water. Samples, 5 ml at each time-point, were taken without media replacement at 1, 2, 4 and 8 hours.

The resulting cumulative dissolution profile, based upon a theoretical percent active added to the formulations is presented in tabulated form below:

| Time (hours) | Theoretical wt % of Active Released Sample A |
|---|---|
| 1 | 20.6 |
| 2 | 32.4 |
| 4 | 49.7 |
| 6 | 63.1 |
| 8 | 74.0 |
| 10 | 82.6 |

Example 3

Three Gastric Retentive (GR™) gabapentin formulas were manufactured utilizing a standard granulation technique. The formulations manufactured are shown in tabulated form below:

| Formulation for Clinical Trial Manufacture | | |
|---|---|---|
| Gabapentin GR8, 300-mg (GR8, 300-mg) | Gabapentin GR6, 300-mg (GR6, 300-mg) | Gabapentin GR8, 600-mg (GR8, 600-mg) |
| 44.76% Gabapentin | 44.76% Gabapentin | 61.11% Gabapentin |
| 21.99% Methocel ® K15M, premium | 16.46% Methocel ® K4M, premium | 7.59% Methocel ® K15M, premium |
| 21.99% Sentry ® PolyOx ® WSR Coagulant, NF FP | 21.99% Sentry ® PolyOx ® WSR 303, NF FP | 27.09% Sentry ® PolyOx ® WSR 303, NF FP |
| 7.49% Avicel ® PH-101, NF | 12.98% Avicel ® PH-101, NF | 0.00% Avicel ® PH-101, NF |
| 2.75% Methocel ® E5, prem. | 2.75% Methocel ® E5, prem. | 3.22% Methocel ® E5, prem. |

-continued

Formulation for Clinical Trial Manufacture

| Gabapentin GR8, 300-mg (GR8, 300-mg) | Gabapentin GR6, 300-mg (GR6, 300-mg) | Gabapentin GR8, 600-mg (GR8, 600-mg) |
|---|---|---|
| 1.00% Magnesium Stearate, NF | 1.00% Magnesium Stearate, NF | 1.00% Magnesium Stearate, NF |
| 670-mg (Tablet weight) 0.3937" × 0.6299" Mod Oval | 670-mg (Tablet weight) 0.3937" × 0.6299" Mod Oval | 982-mg (Tablet weight) 0.4062" × 0.75" Mod Cap |

Gabapentin was obtained from Plantex U.S.A. (Englewood Cliffs, N.J.). Methocel® brand hydroxypropyl methylcellulose (also known as hypromellose), and Sentry® PolyOx® brand polyethylene oxide were obtained from Dow Chemical (Midland, Mich.). Methocel E5, premium is a USP type 2910 hydroxypropyl methylcellulose with number average molecular weight of on the order of 6000-8000 and a viscosity of 5 cps as a 2% aqueous solution at 20° C. Methocel® K4M and Methocel® K15M are USP type 2208 hydroxypropyl methylcellulose with viscosities of 4000 cps and 15,000 cps, respectively, as a 2% aqueous solution at 20° C., and number average molecular weights on the order of 80,000 and 100,000, respectively. Sentry® PolyOx® WSR 301, NF FP, Sentry® PolyOx® WSR Coagulant, NF FP and Sentry® PolyOx® WSR 303, NF FP have viscosity-average molecular weights of approximately 4,000,000, 5,000,000 and 7,000,000, respectively. Avicel PH-101, NF is microcrystalline cellulose supplied by FMC Corporation (Philadelphia, Pa.). Magnesium stearate, NF was supplied by Spectrum Quality Products (New Brunswick, N.J.).

The dissolution profiles, as determined by USP Apparatus I (100 rpm) in modified simulated gastric fluid, for three prototypes Ge™ formulations are shown in FIG. 1.

Example 4

Figure 2:
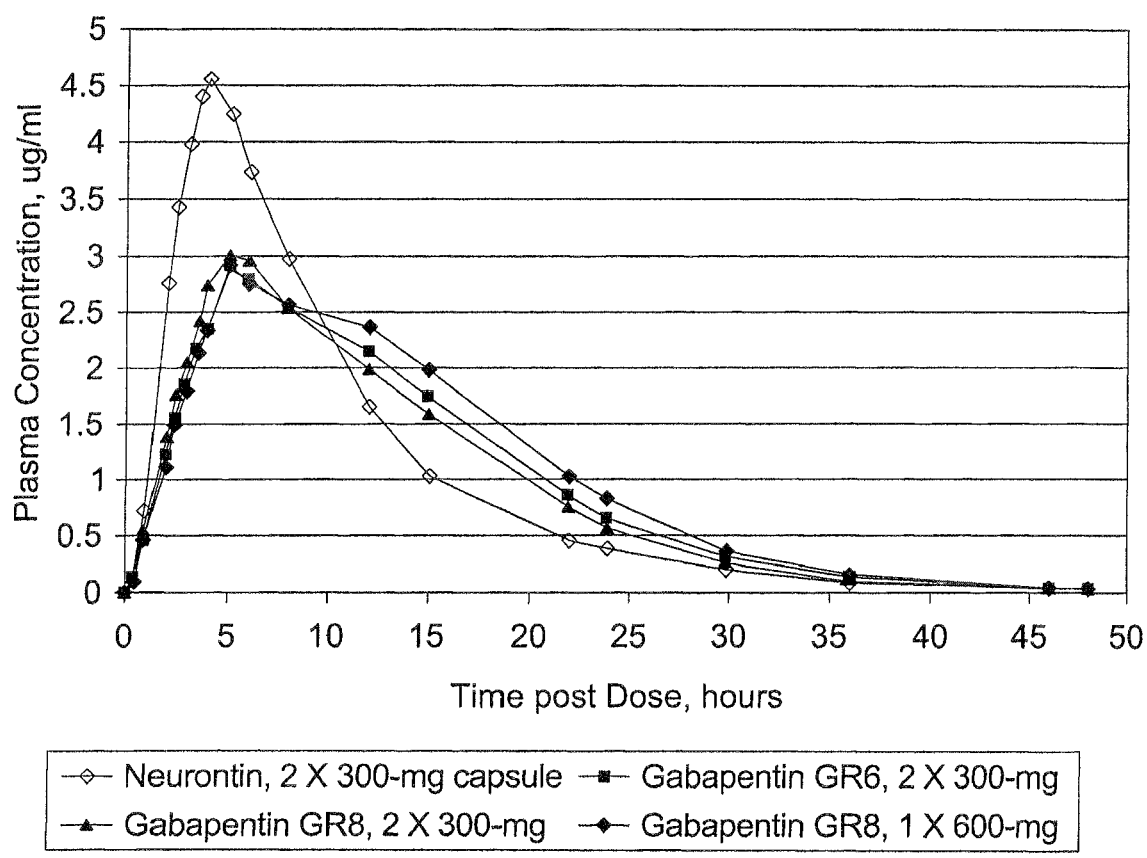
FIG. 2 illustrates the average plasma profiles of three GR™ formulations and Nuerontin.

The pharmacokinetic profiles of the three formulations described in Example 3, administered as a 600-mg dose, were compared to Neurontin® immediate release 300-mg capsule in a randomized four-way cross-over experiment involving 15 healthy volunteers. Each subject was administered treatment of 600-mg gabapentin as one of the three GR™ formulations (1×600-mg tablet or 2×300-mg tablet) or Neurontin® capsules (2×300-mg) within 5 minutes of completing a high fat breakfast (FDA breakfast). Plasma samples were taken up to 48 hours post-dose. FIG. 2 illustrates the average plasma profile for the four treatments administered, and the pharmacokinetic data are summarized in tabulated form below.

Gabapentin Plasma Data - Average for 15 Subjects

| Dosing | | $AUC_{mf}$[#] ((ug/ml) * hr) | $C_{max}$[#](ug/ml) | $T_{max}$ (hours) |
|---|---|---|---|---|
| Nerontin ®, 300-mg 2 X capsules | Mean: % CV: | 46.65 19.0 | 4.72 20.2 | 3.93 15.1 |
| GR6, 300-mg 2 X tablets | Mean: % CV: | 44.43 34.9 | 2.97 29.7 | 6.63 45.1 |
| GR8, 300-mg 2 X tablets | Mean: % CV: | 41.84 34.4 | 3.10 26.2 | 5.63 34.9 |
| GR8, 600-mg 1 X tablet | Mean: % CV: | 48.01 26.8 | 3.13 18.7 | 7.13 42.2 |

[#]Geometric Mean and Geometric % CV are reported here

As demonstrated in FIG. 2 and in tabulated form above, GR™ formulations demonstrate sustained release with a lower maximum plasma concentration and a larger value for the time of the maximum concentration compared to the immediate release capsules without loss in the bioavailability as measured by the plasma $AUC_{inf}$.

Each of the patent applications, patents, publications, and other published documents mentioned or referred to in this specification is herein incorporated by reference in its entirety, to the same extent as if each individual patent application, patent, publication, and other published document was specifically and individually indicated to be incorporated by reference.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A dosage form, comprising:
   a matrix comprising gabapentin, wherein upon ingestion of the dosage form by a human subject gabapentin is released from the matrix into the upper gastrointestinal tract over about 5-12 hours at a rate sufficient to achieve a lower maximum plasma concentration than that provided by an immediate release dosage form comprising an equal amount of gabapentin, and bioavailability of gabapentin is at least 80% of that provided by the immediate release dosage form comprising an equal amount of gabapentin as measured by the area under the plasma concentration-time curve, $AUC_{inf}$.

2. The dosage form of claim 1, wherein the time to reach maximum plasma concentration is at least 5.6 hours±34.9%.

3. The dosage form of claim 1, comprising a dose of gabapentin of between about 300-600 mg.

4. The dosage form of claim 1, wherein the matrix is a polymer matrix.

5. The dosage form of claim 4, wherein the polymer matrix is comprised of a swellable, hydrophilic polymer.

6. The dosage form of claim 5, wherein the gabapentin is released from the polymer matrix by diffusion.

7. The dosage form of claim 1, wherein the gabapentin is released from the matrix at a rate sufficient to achieve a maximum plasma concentration of at least about 3 µg/mL.

8. The dosage form of claim 1, wherein the ratio of the maximum plasma concentration to the plasma concentration at 15 hours after administration is no more than about 2.

9. A dosage form, comprising:

a matrix comprising 300 mg or 600 mg gabapentin, wherein upon ingestion by a human subject of one 600 mg dosage form or upon ingestion of two 300 mg dosage forms gabapentin is released from the matrix into the upper gastrointestinal tract over about 5-12 hours at a rate sufficient to achieve a lower maximum plasma concentration than that provided by an immediate release dosage form comprising an equal amount of gabapentin, and bioavailability of gabapentin is at least 80% of that provided by the immediate release dosage form comprising an equal amount of gabapentin as measured by the area under the plasma concentration-time curve, $AUC_{inf}$.

10. The dosage form of claim 9, wherein the time to reach maximum plasma concentration is at least 5.6 hours±34.9%.

11. The dosage form of claim 9, wherein the matrix is a polymer matrix.

12. The dosage form of claim 11, wherein the polymer matrix is comprised of a swellable, hydrophilic polymer.

13. The dosage form of claim 12, wherein the gabapentin is released from the polymer matrix by diffusion.

14. The dosage form of claim 9, wherein the gabapentin is released from the matrix at a rate sufficient to achieve a maximum plasma concentration of at least about 3 µg/mL.

15. A method of treating a condition responsive to a therapeutic dose of gabapentin, comprising:

orally administering to a human subject a dosage form comprising a matrix comprising gabapentin, wherein upon ingestion of the dosage form gabapentin is released from the matrix into the upper gastrointestinal tract over about 5-12 hours at a rate sufficient to achieve a lower maximum plasma concentration than that provided by an immediate release dosage form comprising an equal amount of gabapentin, and bioavailability of gabapentin is at least 80% of that provided by the immediate release dosage form comprising an equal amount of gabapentin as measured by the area under the plasma concentration-time curve, $AUC_{inf}$.

16. The method of claim 15, wherein the time to reach maximum plasma concentration is at least 5.6 hours±34.9%.

17. The method of claim 15, wherein the matrix is a polymer matrix.

18. The method of claim 17, wherein the polymer matrix is comprised of a swellable, hydrophilic polymer.

19. The method of claim 15, wherein the condition is pain.

20. The method of claim 15, wherein the condition is neuropathic pain.

21. The method of claim 15, wherein the gabapentin is released from the matrix at a rate sufficient to achieve a maximum plasma concentration of at least about 3 µg/mL.

22. A method of treating a condition responsive to a therapeutic dose of gabapentin, comprising:

orally administering to a human subject a dosage form comprising a matrix comprising gabapentin, wherein gabapentin is released from the matrix into the upper gastrointestinal tract over about 5-12 hours at a rate sufficient to achieve a longer time to the maximum plasma concentration than that provided by an immediate release dosage form comprising an equal amount of gabapentin, and bioavailability of gabapentin is at least 80% of that provided by the immediate release dosage form comprising an equal amount of gabapentin as measured by the area under the plasma concentration-time curve, $AUC_{inf}$.

23. The method of claim 22, wherein the matrix is a polymer matrix.

24. The method of claim 23, wherein the polymer matrix is comprised of a swellable, hydrophilic polymer.

25. The method of claim 22, wherein the condition is pain.

26. The method of claim 25, wherein the condition is neuropathic pain.

27. The method of claim 22, wherein the gabapentin is released from the matrix at a rate sufficient to achieve a maximum plasma concentration of at least about 3 µg/mL.

* * * * *